United States Patent [19]

Marcantonio

[11] Patent Number: 5,033,095
[45] Date of Patent: Jul. 16, 1991

[54] SCANNING IMAGE ANALYZER FOR ACCUMULATING QUANTIFIABLE CONTAMINANTS OF WEBS

[76] Inventor: Jeffrey J. Marcantonio, 21 Saratoga Ave., South Glens Falls, N.Y. 12803

[21] Appl. No.: 252,798

[22] Filed: Sep. 30, 1988

[51] Int. Cl.⁵ .......................... G06K 9/00; H04N 7/18; G01N 21/00; G01N 21/88
[52] U.S. Cl. ........................................ 382/8; 358/106; 356/237; 250/572; 377/11
[58] Field of Search ............................. 382/8; 358/106; 356/237, 238, 430, 431; 377/10, 11; 250/559, 571, 572

[56] References Cited

U.S. PATENT DOCUMENTS

| | | | |
|---|---|---|---|
| 3,389,789 | 6/1968 | Watson et al. | 358/106 |
| 4,402,604 | 9/1983 | Nash | 356/237 |
| 4,428,672 | 1/1984 | Allard et al. | 356/237 |
| 4,661,985 | 4/1987 | Akutsu | 382/8 |
| 4,724,481 | 2/1988 | Nishioka | 358/106 |

OTHER PUBLICATIONS

The New Artek AUTOCOUNT Brochure by Artek Systems Corporation.
"Automatic Image Analysis and Measurement Systems for the Pulp and Paper Industry", by Optomax, Inc., Apr. 1986.

Primary Examiner—Leo H. Boudreau
Assistant Examiner—Michael R. Cammarata
Attorney, Agent, or Firm—Nixon & Vanderhye P.C.

[57] ABSTRACT

A microcomputer based digital analysis system is disclosed which includes a microcomputer and a flatbed optical scanner to analyze test sheets of paper fabricated from a batch of pulp to be tested. A keyboard is utilized by an operator to select one of a predetermined number of reports. After a report is selected, a menu is displayed on a CRT which enables the operator to start the sample tests under the control of the microcompuer. Once the total document is scanned either by operator manipulation or under the control of an automatic document feeder, the microcomputer tabulates the data retrieved during each of the individual sheet tests as necessary to generate the report selected by the operator. The microcomputer processes the image data on a line by line basis. A dot buffer is created having a location for each pixel across the scanned line, wherein numbers are incremented as dots having image data are encountered in the scanned line. A dirt array is also created which contains the sum total of tabulated areas from the dot buffer in pixels for each contiguously connected group of pixels that have values greater than a recognition threshold. The dirt array is a summation array for each speck of dirt detected which stores data representative of the size of the dirt speck.

33 Claims, 6 Drawing Sheets

SCANNING IMAGE ANALYZER FOR ACCUMULATING QUANTIFIABLE CONTAMINANTS OF WEBS

FIELD OF THE INVENTION

This invention relates to a method and apparatus for optical analysis of a material that is manufactured in web form to determine at least one property of the material. More particularly, the invention utilizes a microcomputer based digital analysis system to process image data so as to quantify at least one property of a material manufactured in web form (such as the dirt content in paper) by the measurement and analysis of the intensity of light reflected by the material being analyzed.

BACKGROUND AND SUMMARY OF THE INVENTION

Although the specification focuses on the analysis of paper (and more particularly quantifying the quality of the paper by counting and categorizing the dirt particle content), the apparatus of the present invention may be utilized for analyzing other materials. In this regard, any material manufactured in web form such as viscose, cellulose, cardboard, fabric and other similar materials may also be analyzed by the present invention. The present invention may be advantageously utilized to analyze any material property (such as dirt count) which is quantifiable by the measurement of the intensity of light reflected by the material being analyzed.

Paper is typically formed by spraying pulp fibers onto a web and allowing the fibers to dry. Although pulp processing typically involves filtering the pulp to eliminate contaminants, inevitably varying levels of dirt particles contaminate the processed pulp and degrade the quality of the paper being manufactured.

The degree to which the pulp is contaminated by dirt significantly impacts the applications to which a paper product may be utilized. In this regard, only paper with a relatively low dirt particle count would be considered for use in a hardbound, high quality novel. Alternatively, paper utilized to form sandwich bags may have a relatively higher degree of dirt particle content.

Typically, a paper manufacturer utilizes pulp to initially fabricate a square meter test sheet of paper. The test sheet is then cut into individual sheets, e.g., 8 ½" by 11". These individual sheets are then visually inspected and measured for dirt in accordance with conventional TAPPI T-437 specifications.

A dirt count measurement is then obtained based on a visual comparison of dirt spots shown in the TAPPI specifications with the dirt particle configuration shown on the individual sheets of the square meter sample. In this manner, the inspector selects a size category from the TAPPI specifications which most closely matches the size of the dirt particles found on the sample sheets.

After analyzing each of the individual sheets of the square meter sample, the inspector adds the data obtained from the TAPPI specifications to quantitatively assess how many millimeters of dirt are present on each sheet to ultimately determine the number of square millimeters of dirt in the square meter sample. Thereafter, values are computed which hopefully reflect the dirt present in the square meter sample in parts per million. The parts per million dirt particle value is then utilized by the paper manufacturer to determine whether the pulp is of an acceptable quality.

Because the readings obtained by visual inspection are highly subjective, such readings are inherently inaccurate. Accordingly, the ultimate value obtained for a given test sheet is highly dependent on the individual inspector. Such a value can be expected to vary significantly if a different inspector were to evaluate the same test sheet.

Attempts have been made to automate dirt particle counting and categorizing in the paper industry. One currently available dirt particle counting system was originally designed for counting bacteria cultures.

In currently available particle counting systems, postage stamp size regions of a paper product are sampled and the dirt particle content analyzed for these small regions. Thereafter, such systems project the overall paper quality based on the samples taken. Such systems fail to generate an accurate representation of the dirt particle content of an entire square meter of a paper test sheet since the dirt particles tend to be randomly distributed thereby precluding obtaining a representative sample of small regions. If a large number of dirt particles are distributed in a non-sampled portion of such a test sheet, the particle count projection will not be accurate.

The present invention recognizes that the field of view of such systems may not be adequate to accurately quantitatively analyze the dirt particle content of paper sample on the order of the conventionally inspected one square meter sample size.

The present invention utilizes a microcomputer based digital analysis system which includes a microcomputer and a flatbed optical scanner to analyze test sheets of paper fabricated from a batch of pulp to be tested. A keyboard is utilized by an operator to select one of a predetermined number of reports. After a report is selected, a menu is displayed on a CRT which enables the operator to start the sample tests under the control of the microcomputer.

Once the total document is scanned either by operator manipulation or under the control of an automatic document feeder, the microcomputer tabulates the data retrieved during each of the individual sheet tests as necessary to generate the report selected by the operator.

The microcomputer processes the image data on a line by line basis. A dot buffer is created having a location for each pixel across the scanned line, wherein numbers are incremented as dots having image data are encountered in the scanned line. A dirt array is also created which contains the sum total of tabulated areas from the dot buffer in pixels for each contiguously connected group of pixels that have values greater than a recognition threshold. The dirt array is a summation array for each speck of dirt detected which stores data representative of the size of the dirt speck.

BRIEF DESCRIPTION OF THE DRAWINGS

These as well as other objects and advantages of this invention will be better appreciated by reading the following detailed description of the presently preferred exemplary embodiments taken in conjunction with the accompanying drawings of which.

DETAILED DESCRIPTION OF THE DRAWINGS

Figure 1:
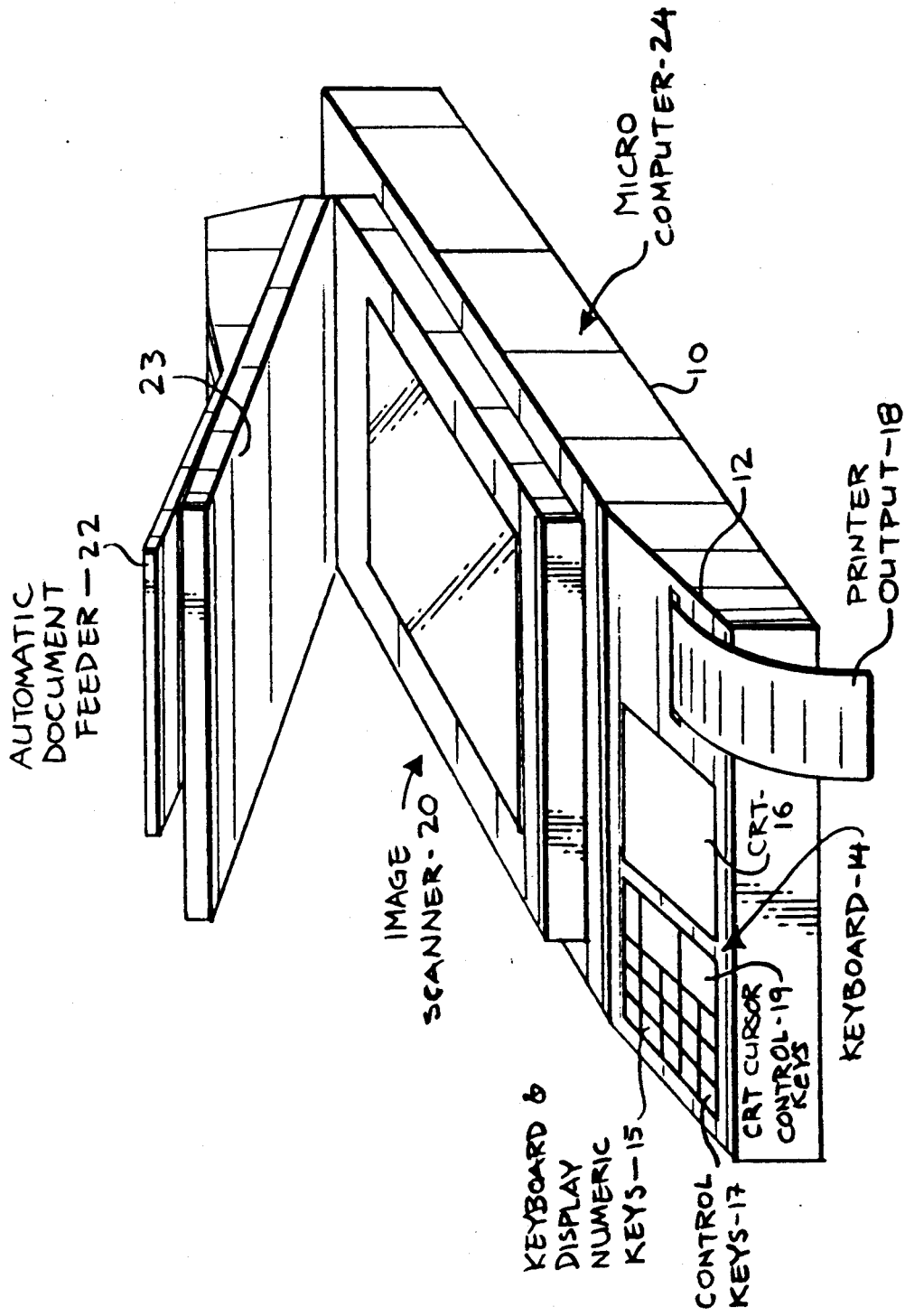
FIG. 1 is a perspective view of an exemplary scanning image analyzer in accordance with the present invention.

FIG. 1 is a perspective view of an exemplary embodiment of a scanning image analyzer in accordance with the present invention. The scanning image analyzer is shown as a desktop lab instrument housed in a compact, low profile metal cabinet housing 10. The image analyzer is advantageously designed to be placed on a desk top in a paper mill laboratory where space is typically limited.

The housing 10 includes an angularly disposed front panel 12 which provides easy operator access to the keyboard 14, cathode ray tube (CRT) display 16 and printer output 18. The keyboard 14, CRT 16, and printer output 18 serve as the image analyzer's operator interface permitting the operator to interact with microcomputer 24 (which is disposed within housing 10) via keyboard 14 and the menus displayed on CRT 16.

Keyboard 14 may, for example, include numeric keys 15, function control keys 17, and CRT cursor control keys 19 (which are utilized to permit an operator to move a cursor to enable selection of an entry in a displayed menu). The printer output 18 permits the operator to receive one of a number of selectable dirt particle reports which are selected of control keys 17. The keys on keyboard 14 are scanned by microcomputer 24 in a manner which is conventional.

The scanning image analyzer shown in FIG. 1 also includes an image scanner 20 disposed above microcomputer 24 on the top portion of housing 10. An automatic document feeder 22 having a reflective backing 23 is hingedly coupled to image scanner 20.

Figure 2:
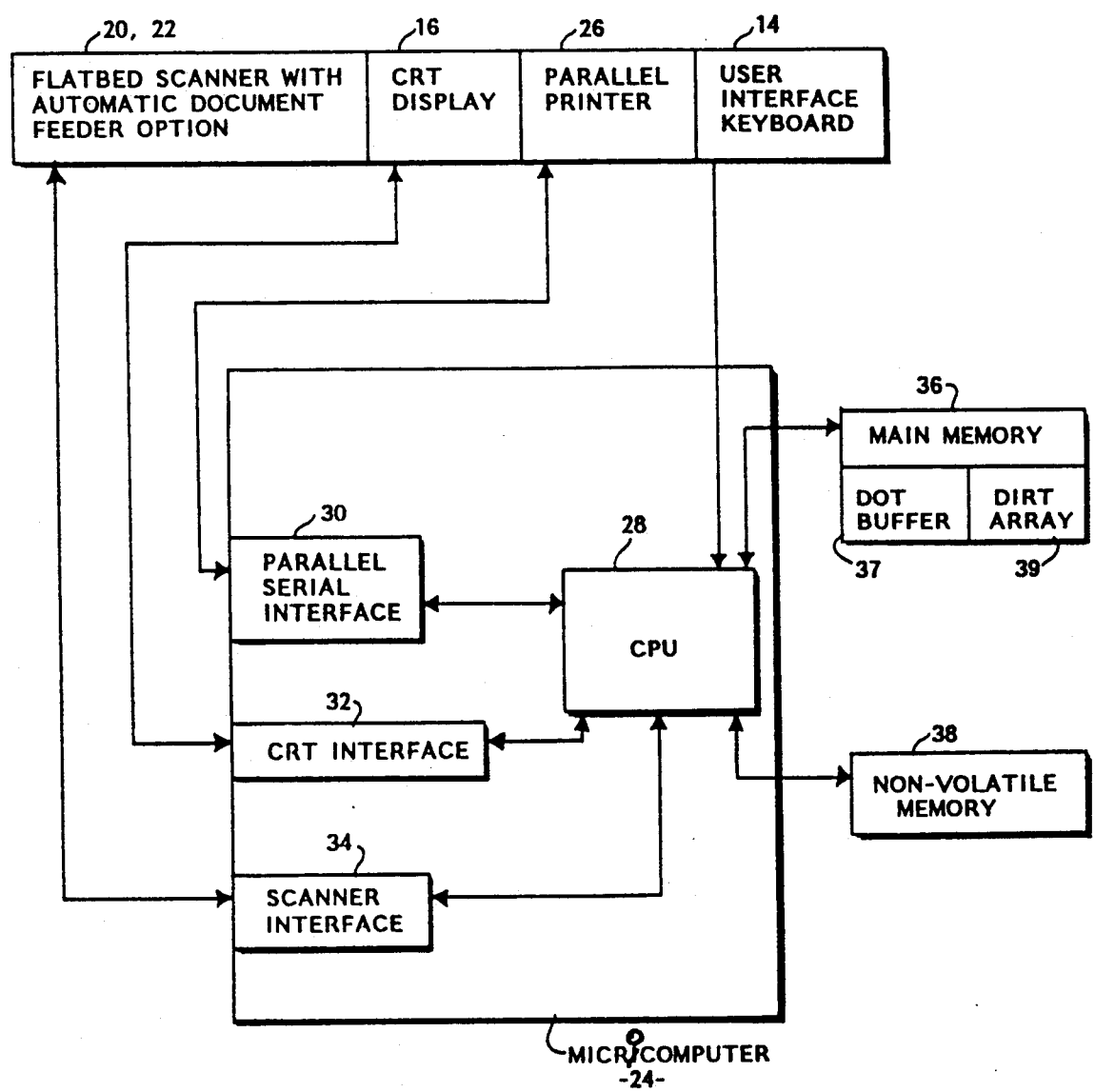
FIG. 2 is a block diagram of the scanning image analyzer shown in FIG. 1.

FIG. 2 is a schematic block diagram of the scanning image analyzer shown perspectively in FIG. 1. Components in FIGS. 1 and 2 which are identical are identically labelled.

The flatbed scanner 20 with the automatic document feeder 22 may, for example, be a Panasonic FXRS-506 flatbed scanner. This scanner includes a fluorescent reflective light source and a linear array of charge coupled device (CCD) photosensors (not shown).

When the automatic document feeder 22 is not in use, the flatbed scanner operates in an individual sheet scanning mode. In this regard, the light source, and photosensor array are moved in concert to scan one of, for example, fifteen sample sheets.

The automatic document feeder 22 includes a white or otherwise light reflecting portion 23 which rests against the test sheet on the image scanner 20. The light from the flatbed scanner's light source is reflected from backing 23 and the intensity of such reflected light is picked up by a photosensor array having a 400 dots per inch spacial resolution.

The intensity level data detected by flatbed scanner 20 is sent to the scanner interface board 34 associated with the microcomputer 24. The scanner interface 34 may be the conventional interface which is provided with the Panasonic FXRS-506 flatbed scanner. The scanner interface 34 includes an analog to digital converter hardware module as well as a software interface for interfacing with microcomputer 24.

When the flatbed scanner 20 is utilized in conjunction with the automatic document feeder 22, the illumination source and photosensor array remain stationary and the individual sample sheets are moved by the document feeder 22 passed the illumination source and photosensor array to provide the relative motion necessary to scan the document. The 400 dots per inch resolution provided by the flatbed scanner 20 permits recognition of extremely small dirt specks with enough resolution to determine that the data, in fact, represents a dirt particle rather than background noise.

Microcomputer 24 which is coupled to flatbed scanner 20 and the document feed 22 via the scanner interface 34 may, for example, be an IBM PC/AT compatible microcomputer. Microcomputer 24 includes an associated main memory 36 having 640K storage locations. Microcomputer 24 is also coupled to a nonvolatile memory 38 which initially stores the scanning analyzer applications programs and which may, for example, be a static RAM virtual disk. As will be explained in detail below in conjunction with FIG. 3, main memory 36 may include a set of locations defining a dot buffer memory 37 and a dirt array 39.

Microcomputer 24 also includes a central processing unit (CPU) 28 which is the microcomputer's arithmetic and logic unit. CPU 28 is coupled to a conventional parallel/serial interface 30 which, for example, interfaces with parallel printer 26 (which may be, for example, a Telepar Model T-40). Interface 30 also provides the capability of serially interfacing with, for example, other processing units if desired for distributing processing tasks.

CPU 28 is also coupled to a conventional display controller which is shown in FIG. 2 as CRT interface 32 and, which may, for example, be an RS-170 interface. The display controller 32 is coupled to CRT 16, which may be a Javelin BWM-9 raster scan display.

As is typical with IBM PC compatible computers, microcomputer 24 includes expansion slots, 30, 32, 34, etc., for interfacing with various peripheral devices which are in turn coupled to a CPU motherboard 28.

The scanning image analyzer shown in FIGS. 1 and 2, is typically operated to analyze a 1 square meter sample of paper fabricated from a batch of pulp to be tested. The 1 square meter sample is typically either obtained by taking a 1 meter sample from a paper fabricating machine or from individual sheets which are made from pulp slurry to test the quality of the pulp.

If the thickness of the paper to be tested is within a predetermined thickness range, then the automatic document feeding option may be utilized. Thus, the 1 square meter sample may be cut into, for example 15 individual sheets and then fed as a package into automatic document feeder 22.

Thereafter, keyboard 14 is utilized to select one of a predetermined number of reports. In this regard, an operator may select printing out the dirt particle count in parts per million at printer output 18. Alternatively, each individual dirt speck detected can be categorized as to size, which sizes are tabulated for the operator. After a report is selected, a menu is displayed on CRT 16 which enables the operator to start the sample tests under the control of microcomputer 24.

If a paper sample is too large to fit in the automatic document feeder 22, an operator can manipulate the paper by hand. After selecting a report to be printed on output printer 18, the operator may start a test on one individual sheet at a time as opposed to initiating a sequence of tests for each of the documents placed in automatic document feeder 22. After completing a test on one portion of a sheet, the operator then manipulates the sheet by hand to a new portion of the sample to be scanned.

Once the total document is scanned either by operator manipulation or under the control of automatic document feeder 22, microcomputer 24 tabulates the data retrieved during each of the individual sheet tests as necessary to generate the report selected by the operator. In this regard, a report may be generated categorizing the dirt particle sizes which were measured and indicating the number in each category in, for example, a histogram format, if such a report were chosen during the report selection entry mode.

Figure 3:
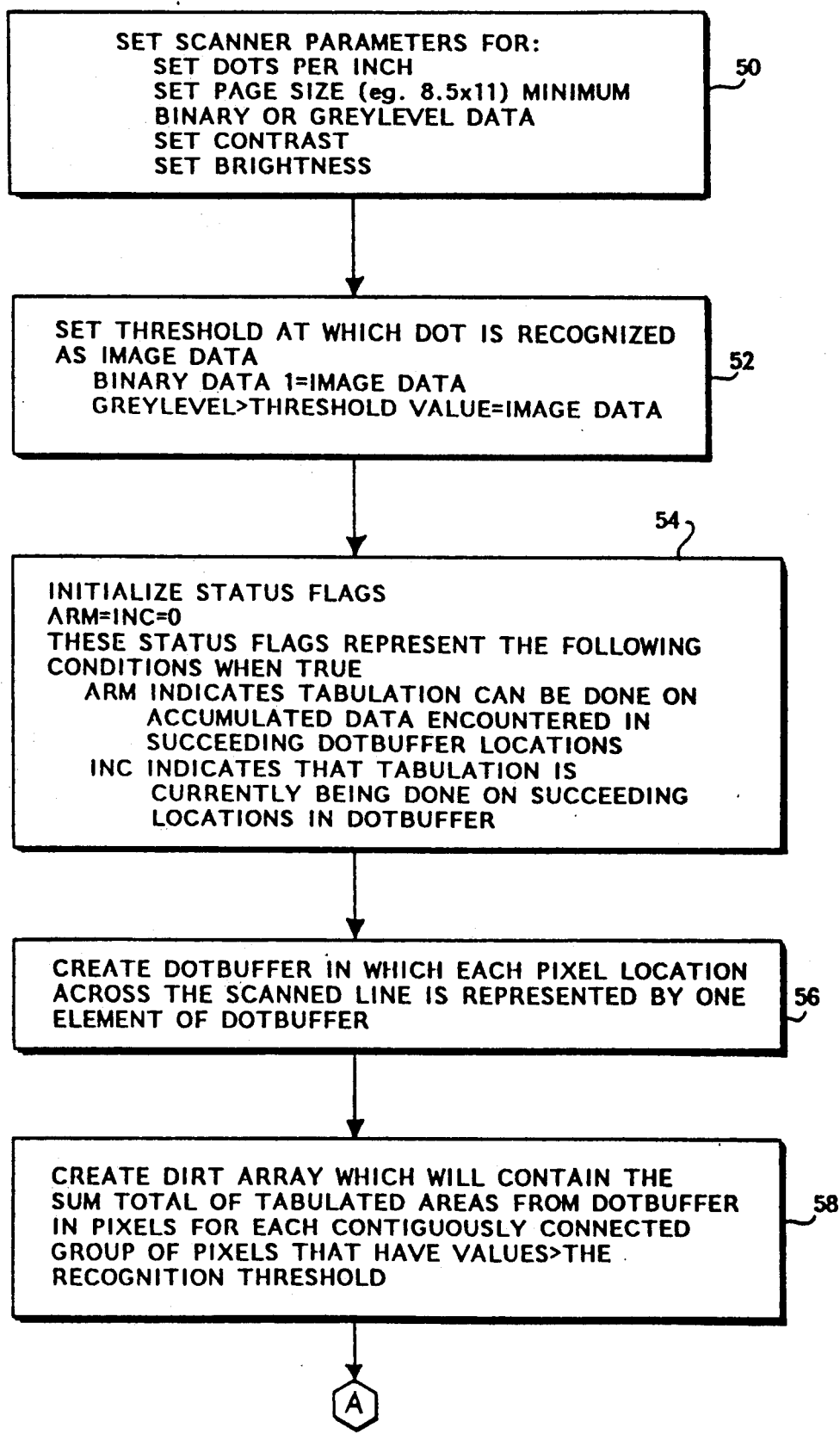
FIGS. 3 through 6 are a flowchart delineating the sequence of operations performed by the microcomputer shown in FIG. 2.
Figure 4:
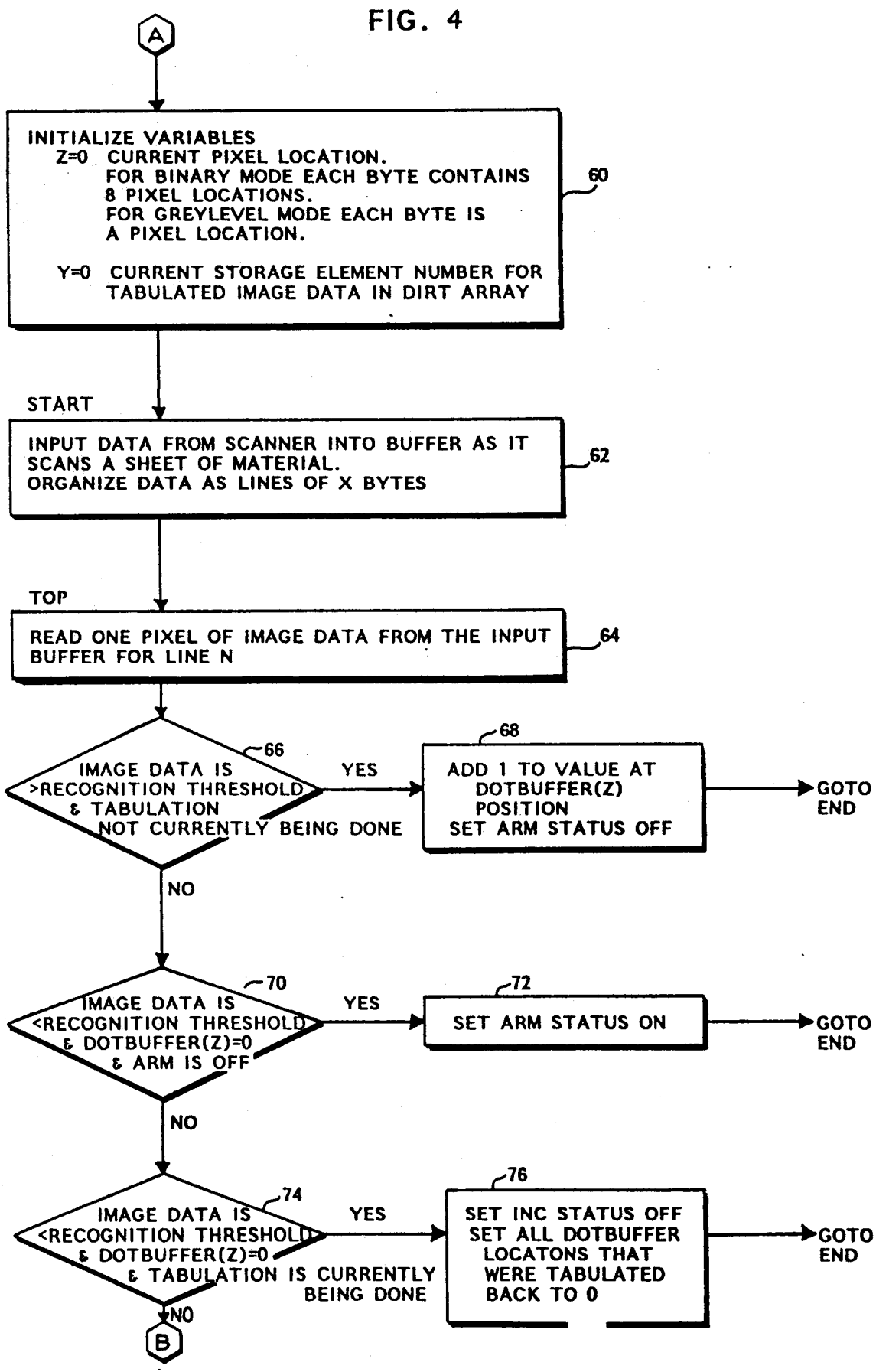
Figure 5:
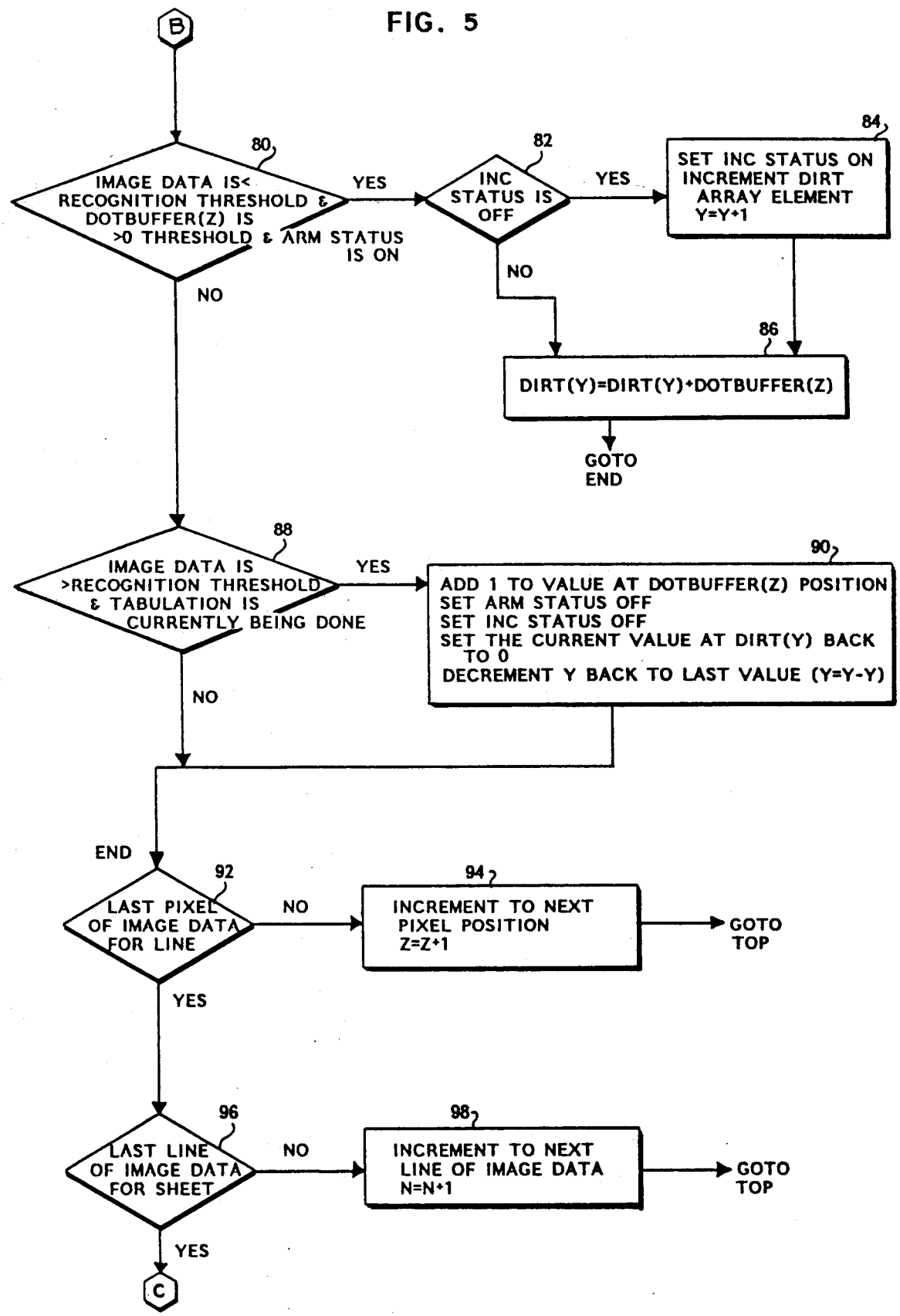
Figure 6:
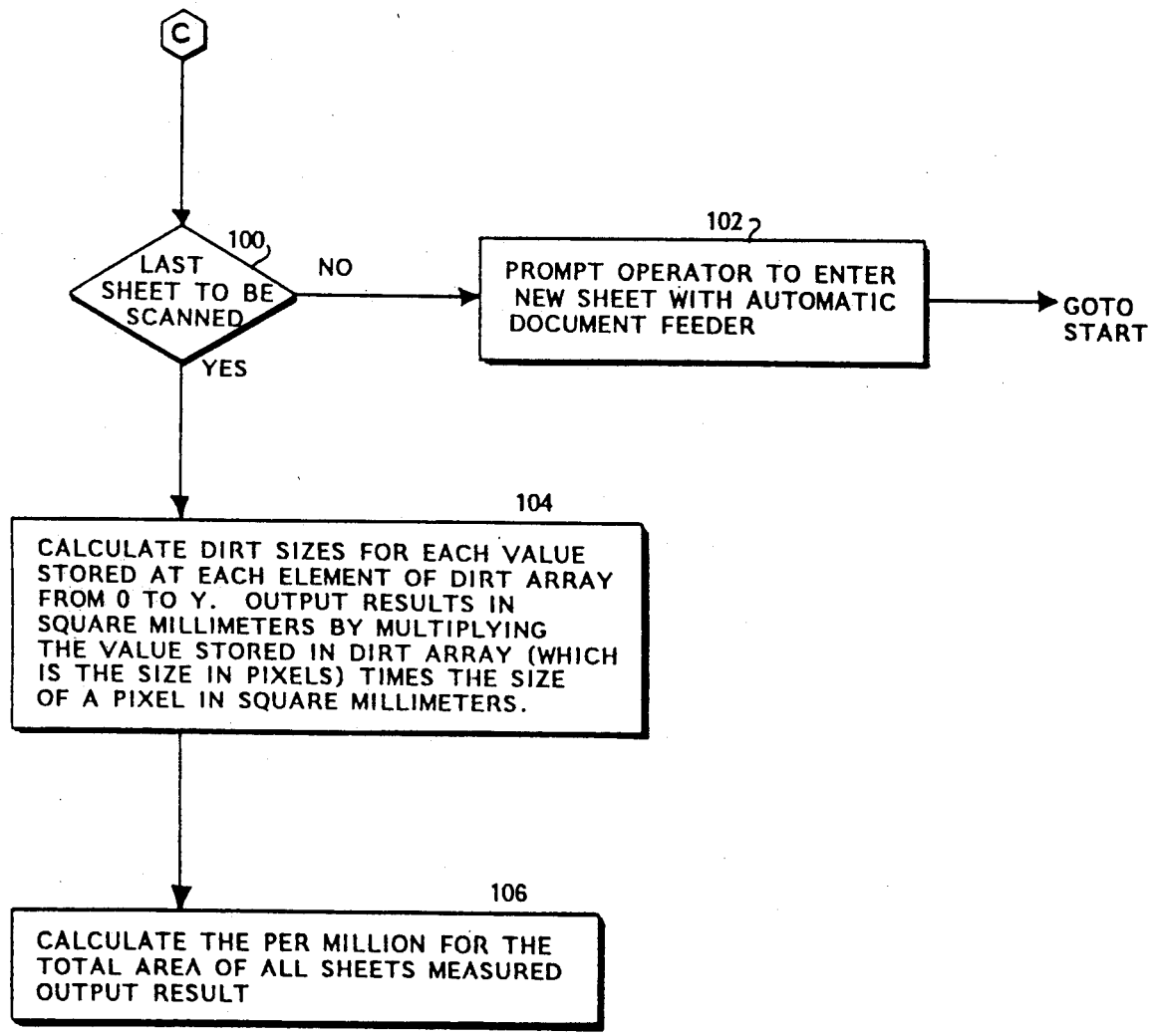

FIGS. 3–6 are a flowchart of the sequence of operations performed by computer 24 in controlling the scanning image analyzer to recognize and tabulate sizes of dirt particles in paper in the exemplary embodiment of the present invention. Turning first to FIGS. 3 and 4, blocks 50 through 60 show a sequence of initializing processing steps performed before input data from optical scanner 20 is processed by microcomputer 24.

Initially, as indicated in FIG. 3 at block 50, various parameters are set for flatbed scanner 20. For example, parameter setting control signals are transmitted from microcomputer 24 to flatbed scanner 20 which set the number of dots per inch and the page size that ill be scanned. In accordance with the present invention, as noted above, in order to obtain a complete and representative sample of test sheet image data, the page size is set to at least a minimum of size of, for example, 8½ inches × 11 inches.

Additionally, the scanner 20 is sent a control signal indicating that the data to be transmitted to microcomputer 24 must be in the form of an indication of black or white data for each pixel (i.e., binary data) or grey level data (e.g., an indication of one of sixteen grey level gradations). The binary or grey level data is then analyzed by microcomputer 24 to identify the presence of an opaque speck in the web material under test which in the exemplary embodiment indicates the presence of a dirt speck in paper. Additionally, microcomputer 24 sets the contrast and brightness of the scanner 20 so that the scanner picks up the smallest dirt speck in the paper desired to be detected.

After the scanner parameters are set, the threshold at which a dot is recognized is set (52). If binary data had been selected in block 50, then the scanner 20 is automatically set at a threshold of, for example, a mid-range grey level setting. If the grey level data mode is selected, then a predetermined grey level threshold is set.

In either case, the threshold setting represents the minimum value at which a dot is recognized as valid image data. If the detected value for a pixel location is below the threshold, then for that particular dot no valid image data is recognized which might indicate the presence of a dirt speck or other anomaly in the paper.

As indicated at block 54, various status flags utilized in the routine are initially set to zero. The significance of these status flags will become apparent after a review of the figures which follow.

These status flags represent the presence or absence of predetermined conditions in the routine. In this regard, the "ARM" status flag, if set, indicates that previous conditions have "armed" the routine so that the next time the routine encounters image data accumulated from a previous line, it can begin to tabulate such data. This condition is set when there is no image data in the presently scanned line, which is part of the immediately preceding scanned last line.

As will be explained further below, two lines are processed as a pair. After a line is read in which there is image data, data is stored in dot buffer memory 37 which may, for example, be located in memory 36. Thereafter, the next line, is likewise scanned and placed in the dot buffer. In the dot buffer 37, line data is stored in parallel corresponding locations. The locations in the pair of lines are checked to determine if the present line image data includes data which is a continuation of the data from the previous line.

If the current line has no data which connects to (or is a part of) the previous line, then the system is in a condition to begin tabulation and the "ARM" status indicator is turned on. Once the "ARM" status is triggered, as values in the dot buffer 37 which are greater than zero are detected, those values are then summed or tabulated.

The "INC" status condition indicates that a tabulation is currently being done on succeeding locations in the dot buffer 37. Thus, the "INC" status indicator being in a "1" condition, indicates that successive dots in the dot buffer are being actively summed.

The ARM and INC status conditions are checked during the routine as will be described further below to determine, for example, whether the routine is in the process of tabulating at a point in time when valid image data is detected. This detection of valid data indicates that the current tabulation will not yield a valid result and accordingly, must be abandoned. Under such circumstances, the just detected image data must be taken into account in the tabulation. Only when an entire line of image data has no valid image data in locations corresponding to the previous line can dot buffer locations be tabulated to result in tabulated data defining a complete dirt speck. It is noted that as data is tabulated, data stored in the dot buffer is erased to preserve memory locations. Such erased data, however, is restored if the current tabulation is abandoned.

After the status flags are initialized as per block 54, a dot buffer memory 37 is created in which each pixel location across the scanned line is represented by one element of the dot buffer 37 (56). Thus, an array is created having a location for each pixel across the scanned line, wherein numbers are incremented as dots having image data are encountered in the scanned line.

Thereafter, as per block 58, dirt array 39 is created, for example, in memory 36 which contains the sum total of tabulated areas from the dot buffer 37 in pixels for each contiguously connected group of pixels that have values greater than the recognition threshold. Thus, the dirt array 39 is a summation array for each speck of dirt detected which stores data representative of the size of the dirt speck. The dirt array 39 includes a pointer which may be incremented such that it points to the next piece of dirt. The dirt array 39 has as many entries as the number of dirt specks detected.

As a final initializing step, as indicated at block 60, a variable Z is initially set equal to zero. Z represents the current pixel location in the dot buffer 37. In the binary operating mode, each byte read in from the scanner 20 contains 8 pixel locations. Each bit in the byte corresponds to a pixel. If the bit is a "1", then the pixel is above the binary threshold which has been set as explained in conjunction with block 52. If the bit is a "0", then the threshold value for valid image data has not been exceeded. In the grey level operating mode, each byte represents a single pixel location and defines the grey level associated with the pixel location.

Additionally, as indicated at block 60, a variable Y is set equal to zero. The variable Y represents the current storage element number for tabulated image data in the dirt array 39 which was created as described above at block 58. Thus, the variable Y is a pointer to the current storage element in the dirt array 39.

After taking care of all the necessary initializing operations, input data from the scanner 20 is then read into an input buffer as the scanner 20 scans the sheet of material. The data read into the input buffer is then organized into N lines of X bytes (62). By way of example only, a full line of data may be 425 bytes in the binary operating mode and 1700 bytes in the grey level operating mode.

Thereafter, in accordance with block 64, a portion of the routine labeled "TOP" is entered in which one pixel of image data is read from the input buffer for the current line being processed (64). The pixel of image data which is read is then compared to the recognition threshold. A check is then made to determine whether the recognition threshold has been exceeded and if tabulation is not currently being done (66).

If both these conditions are satisfied, then one is added to the value in the current dot buffer location Z and the ARM status is set to the off or "zero" state (68). At this point in the routine, the system should not be "armed" to tabulate since no image data is in the dot buffer 37 as yet.

After the processing at block 68 (presuming the condition specified at block 66 is satisfied), the routine jumps to block 92 (which is labelled "END") and a check is made to determine whether the pixel being processed is the last pixel of image data for the line (92). If not, then the current pixel location is incremented to the next pixel location, as indicated at block 94, after which the routine branches back to block 64.

At block 64 another pixel of image data is read from the input buffer and a check is again made at block 66 as described above. If the condition identified in block 66 is not met, then a check is made at block 70 to determine whether the detected image data is less than the recognition threshold. Additionally, a check is made of the current pixel location Z to determine whether any previous image data information from previous lines are stored in that current pixel location. Additionally, a check is made to determine whether the "ARM" status indicator is off.

If each of the three conditions defined in block 70 are satisfied, then the ARM status indicator is turned on (72). As indicated above, the ARM status indicator places the system in a condition where tabulation can be done on accumulated data encountered in succeeding dot buffer locations. Thereafter, the routine branches to block 92 where a check is made to determine whether the last pixel of image data for the line has been processed and the routine increments to the next pixel as per block 94. Thereafter, the next pixel is read from the input buffer as per block 64.

After retrieving the next pixel at block 64, presuming that the above-described checks at blocks 66 and 70 are negative, a further check is made at block 74. At block 74, if the image data is less than the recognition threshold and if the current dot buffer location Z is equal to zero and if tabulation is currently being done on a previous pixel, then a determination has in effect been made that a dirt speck has been fully defined since a dot buffer location has been encountered where there is nothing stored therein.

Under such circumstances, the "INC" status indicator is turned off and all dot buffer locations that were tabulated are set back to zero (76). The routine then branches to block 92 where a check is again made to determine whether the last pixel of image data for the line has been encountered, after which the pixel position is incremented (94) and the next pixel of image data is read from the input buffer (64).

After retrieving the next pixel from the input buffer at block 64, and presuming that the checks at blocks 66, 70, and 74 are negative, a further check is made at block 80. As indicated at block 80, if the image data is still less than the recognition threshold, and if the current dot buffer location has a value therein greater than zero, and if the ARM status is on, a further check is made at block 82.

It is noted that, when the current dot buffer location has a value stored therein greater than zero, pixels were found in the previous line data which were greater than the recognition threshold at a corresponding location to the current location Z. The value in the dot buffer location Z thus indicates in how many lines the dirt speck has been detected up to this point in the routine. Since block 80 also requires a determination that there is no current image data which exceeds the recognition threshold for the pixel being processed, then a check must be made to determine whether the INC status is off which means the tabulation is not currently being done (82).

If the INC status is off, then as indicated at block 84 the INC status is turned on and the dirt array element is incremented from the current position (Y) to the next position (Y + 1). In this manner, the dirt array element pointer will point to the next element in the dirt array.

If the check at block 82 is negative or after the processing in block 84, the current storage element in the dirt array has its contents incremented by the contents of the dot buffer location Z (86) to thereby generate a sum total of the tabulated area from the dot buffer. Thereafter, the routine branches to block 92 at which point a check is made to determine whether the last pixel of the image data for the line has been reached. If not, the next pixel of image data is retrieved from the input data as per blocks 94 and 64. It is noted that the dirt array will ultimately be incremented to reflect the total number of dirt particles found in the paper. The value contained in each of the locations of the dirt array reflects the size of each of the associated dirt particles.

If the conditions checked at block 66, 70, 74 and 78 are each negative then a further check is made at block 88. As per block 88, if the image data is greater than the recognition threshold and if tabulation is currently being done, then the routine performs the processing functions defined in block 90.

The check at block 88 indicates that the routine is in the middle of tabulating a piece of dirt and a dot is discovered directly underneath one of the locations in the dot buffer being tabulated. This image data must be added into the tabulation. Accordingly, if the check at block 88 is positive, then the current tabulation must be abandoned. If negative, the routine proceeds to block 92. If the check at block 88 is positive the previous values must be restored. Initially, at block 90 the current dot buffer location is incremented to reflect the image data that was detected at block 88, which was greater than the recognition threshold. Additionally, the ARM status is turned off to indicate that the routine is not presently armed to tabulate. The INC status is turned off to indicate that the routine is not currently tabulating. Additionally, the current value of the dirt array at location Y (dirt (y)) is set back to zero to thereby eliminate the currently tabulated value for location Y since it is not valid.

Finally, at block 90 the pointer which points to the current dirt array location is set back to point to the last dirt array location, i.e., the dirt location Y is set equal Y − 1. By decrementing the current dirt array location back to the last value in effect recognizes that the routine does not as yet realize that there is, in fact, another completely defined dirt speck on the paper.

A check is then made at block 92 to determine whether the current pixel is the last pixel of image data for a line. If so, then a further check is made to determine whether the current line is the last line of image data for the sheet (96). If the last line has not yet been reached, then the routine increments to the next line of image data (98) and branches back to block 64 to read one pixel of data from the input buffer for the new line N.

If the check at block 96 indicates that all lines of the sheet have, in fact, been scanned, then a check is made to determine whether the current sheet is the last sheet to be scanned (100). If not, then a message is displayed to the operator to manually enter a new sheet or feed a new sheet into the automatic document feeder (102). The routine then branches back to block 62.

If the check at block 100 indicates that the last sheet has, in fact, been scanned, then the dirt size for each value stored at each element of the dirt array from locations zero to Y is calculated. As indicated at block 104, the calculation yields square millimeters by multiplying the value stored in the dirt array (which is the size and pixels) times the size in pixels in square millimeters. Once the size in square millimeters is calculated for the values stored in the dirt array, a calculation is made to determine the parts per million for the total area of all sheets measured and the resulting calculation is displayed on CRT 16 and/or printed by printer 12 (106).

The flow of control delineated by the flowchart shown in FIGS. 3 through 6 may be implemented by a wide variety of computer programs. An exemplary routine for implementing the flowchart is appended hereto as appendix A.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of determining the value of at least one quantifiable contaminant of a web material utilizing an image scanner and a computer comprising the steps of:
    disposing the web material in operative association with the scanner;
    scanning substantially the entire portion of web material which is in operative association with the scanner to produce image data relating to areas of said quantifiable contaminant;
    feeding said image data from the scanner to the computer on a line by line basis;
    processing said image data by said computer by:
        a. Creating a dot buffer memory for storing a first and a second line of image data, each said line of data relating to each pixel location across a scanned line of web material;
        b. Checking each said location of said stored first line with corresponding locations of said stored second line of image data to determine if the second stored line includes image data which is a continuation of data from said first line;
        c. Forming cumulative data in said first stored line pertaining to areas of quantifiable contaminants in response to said checking; and
        d. Storing each subsequent line of image data fed to said computer as said second line of image data and repeating step c. in response thereto.

2. A method according to claim 1 wherein said scanning step includes the step of providing relative motion between the web material and a light source.

3. A method according to claim 1 wherein said scanning step includes the step of utilizing a flatbed scanner to scan the web material.

4. A method according to claim 1 including the steps of sequentially feeding a plurality of sheets of the web material into operative association with the scanner and determining the value of said at least one quantifiable contaminant based on data obtained from said plurality of sheets.

5. A method according to claim 1, wherein the said at least one quantifiable contaminant being determined is the dirt particle content of the web material.

6. A method according to claim 1, wherein said web material is paper.

7. A method according to claim 1, further including the step of providing an output report identifying the value of said at least one quantifiable contaminant.

8. A method according to claim 1 further including the step of:
    setting scanner parameters by the computer.

9. A method according to claim 8, wherein said setting step includes selecting the format of image data to be grey level data.

10. A method according to claim 1 further including the step of setting the threshold at which image data will be recognized as valid image data.

11. A method according to claim 1, wherein said scanning step includes the step of scanning said web material on a line by line basis.

12. A method according to claim 1, wherein said processing further includes the step of storing said tabulated quantifiable contaminant data in an array memory.

13. A method according to claim 1 including the further processing steps of:
    determining that the value of at least one area of said quantifiable contaminant has been completely determined, and
    tabulating quantifiable contaminant data in response thereto.

14. A method according to claim 1 further including the step of discontinuing said tabulating step if it is subsequently determined that the size of said at least one area of a quantifiable contaminant has not been completely determined.

15. A method according to claim 1, further including the steps of determining whether calculations are currently being performed by the computer and storing an indication of the results of said determining step.

16. A method according to claim 1, further including the step of storing an indication as to whether the currently processed image data is such that a calculation can be done on accumulated image data relating to determining said value.

17. A method according to claim 1 wherein said dot buffer memory is used to store cumulative image data relating to a plurality of scanned lines.

18. A method according to claim 15, further including the step of clearing said dot buffer memory in response to tabulating image data relating to at least one area of a quantifiable contaminant whose size has been completely determined.

19. Apparatus for determining the value of at least one quantifiable contaminant of a web material comprising:
   means for scanning said web material on a line by line basis for generating image data relating to area of said quantifiable contaminant;
   buffer memory means responsive to said scanning means for storing image data relating to at least two sequential scanned lines; each said line of image data relating to each pixel location across a scanned line of web material;
   means responsive to said buffer memory means for determining whether said image data stored in one of said two stored scanned lines is a continuation of image data in the other of said at least two scanned lines;
   means responsive to said means for determining for forming cumulative data in said other of said at least two stored lines pertaining to areas of quantifiable contaminants; and
   control means for causing each subsequent scanned line of image data to be stored in said one of said two stored scanned lines and for causing said means for determining and said means for forming to operate on each said subsequent scanned line of image data.

20. Apparatus according to claim 19 further including:
   means responsive to said means for determining for indicating that the value of at least one area of said quantifiable contaminant has been completely determined; and
   means for tabulating quantifiable contaminant data in response to said means for indicating.

21. Apparatus according to claim 20 wherein the said at least one quantifiable contaminant value being determined is the dirt particle content of the web material.

22. Apparatus according to claim 21 further including means for discontinuing said tabulating if it is subsequently determined that the size of a dirt particle has not been completely determined.

23. Apparatus according to claim 21, further including dirt array memory means coupled to said buffer memory means for receiving data stored in said buffer memory means for storing said tabulated data which is indicative of the size of detected particles in said web material.

24. Apparatus according to claim 19 wherein said means for scanning includes a flatbed scanner.

25. Apparatus according to claim 19, wherein said processing means includes means for setting parameters of said means for scanning.

26. Apparatus according to claim 19, wherein said means for scanning includes means for providing relative motion between the web material and a light source.

27. Apparatus according to claim 19 further including means for feeding a plurality of sheets of the web material into operative association with the means for scanning and means for determining the value of the at least one quantifiable contaminant based on data obtained from said plurality of sheets.

28. Apparatus according to claim 19 wherein said means for processing includes means for setting parameters of said means for scanning.

29. Apparatus according to claim 19 further including means for setting the threshold at which image data will be recognized as valid image data.

30. Apparatus according to claim 19, further including means for indicating whether calculations are currently being performed and means for storing said indication.

31. Apparatus according to claim 19, further including means for storing an indication as to whether the currently processed image data is such that a calculation can be done on accumulated image data relating to determining said value.

32. Apparatus according to claim 21 further including means for utilizing said buffer memory to store cumulative image data relating to a plurality of scanned lines.

33. Apparatus according to claim 32, further including means for clearing said buffer memory in response to tabulating image data relating to a dirt particle whose size has been completely determined.

* * * * *